United States Patent [19]

VandenBerg

[11] Patent Number: Plant 6,773

[45] Date of Patent: May 2, 1989

[54] CHRYSANTHEMUM PLANT NAMED DARE

[75] Inventor: Cornelis P. VandenBerg, Salinas, Calif.

[73] Assignee: Yoder Brothers, Inc., Barberton, Ohio

[21] Appl. No.: 135,296

[22] Filed: Dec. 21, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Dare particularly characterized by its flat capitulum form; spooned anemone capitulum type; white ray floret color; diameter across face of capitulum of up to 14 cm at maturity when grown as a pinched disbudded pot mum, with diameter of anemone cushion of up to 6 cm; uniform eight week photoperiodic flowering response to short days; tall plant height when grown as a pinched pot mum; excellent tolerance to high temperatures; recommended both as disbudded and spray pot mum; and upright and prolific branching pattern.

3 Drawing Sheets

The present invention comprises a new and distinct cultivar of Chrysanthemum, botanically known as *Chrysanthemum morifolium,* Ramat, and referred to by the cultivar name Dare.

Dare, identified as 83815001, was originated from a cross made by Cornelis P. VandenBerg in a controlled breeding program in Salinas, Calif. in 1983.

The female parent of Dare was the cultivar Quills, disclosed in U.S. Plant Pat. No. 4,401. The male parent of Dare was the cultivar Echo, disclosed in U.S. Plant Pat. No. 4,973.

Dare was discovered and selected as one flowering plant within the progeny of the stated cross by Cornelis P. VandenBerg in January of 1984, in a controlled environment in Salinas, Calif.

The first act of asexual reproduction of Dare was accomplished when vegetative cuttings were taken from the initial selection in March of 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Dare are firmly fixed and are retained through successive generations of asexual reproduction.

Dare has not been observed under all possible environmental conditions. The phenotype may vary significantly with variations in environment such as temperature, light intensity, and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Dare, which, in combination, distinguish this Chrysanthemum as a new and distinct cultivar:

1. Flat capitulum form.
2. Spooned anemone capitulum type.
3. White ray floret color.
4. Diameter across face of capitulum of up to 14 cm at maturity when grown as a pinched disbudded pot mum, with diameter of anemone cushion of up to 6 cm.

5. Uniform eight week photoperiodic flowering response to short days.
6. Tall plant height, requiring 0 to 7 long days after pinch prior to short days and 1 to 2 applications of 2500 ppm B-9 SP to attain a flowered plant height of 25 to 35 cm for year-round flowerings when grown as a pinched pot mum.
7. Excellent tolerance to high temperatures.
8. Recommended both as disbudded and spray pot mum.
9. Upright and prolific branching pattern.

The accompanying photographic drawings show typical inflorescence and leaf characteristics of Dare, with the colors being as nearly true as possible with illustrations of this type.

Sheet 1 is a color photograph of Dare grown as a pinched disbudded pot mum.

Sheet 2 is a black and white photograph of three views of the inflorescence of Dare.

Sheet 3 is a black and white photograph showing the upper and under sides of the leaves of Dare at three stages of development (mature, intermediate and immature).

Of the commercial cultivars known to the inventor, the most similar in comparison to Dare is the male parent Echo. Reference is made to attached Chart A, which compares certain characteristics of Dare to the same characteristics of Echo.

Similar traits are capitulum form and type. Dare is clear white, has a more prolific branching pattern, a much larger diameter of capitulum, taller plant height and a faster flowering response to short days than Echo. Dare is recommended as both disbud and spray pot mum, whereas Echo is recommended only as a spray pot mum.

In the following description, color references are made to The Royal Horticultural Society Colour Chart. The clear white color of the ray florets is not represented in the R.H.S. Colour Chart. The color values were determined on plant material grown as a pinched disbudded pot mum in Salinas, Calif. on June 11, 1987.

Classification:

*Botanical.—Chrysanthemum morifolium,* Ramat., cv. Dare.

*Commercial.*—Spooned anemone disbud and spray pot mum.

INFLORESCENCE

A. Capitulum:

*Form.*—Flat.

*Type.*—Spooned anemone.

*Diameter across face.*—Up to 14 cm at maturity. Diameter of anemone cushion up to 7 cm at maturity.

B. Corolla of ray florets:

*Color (general tonality from a distance of three meters).*—White.

*Color (upper surface) (spoon tips).*—White.

*Color (under surface) (tubes).*—White.

*Shape.*—Base tubular, Distal portion open, flattened and spoon like. Spoons are narrow, flat and straight. Spoon length varies from 30% to 60% of the length of the ray floret.

C. Corolla of disc florets (Anemone Cushion):

*Color (mature).*—Closest to 155A with tips closest to 3B.

*Color (immature).*—Closest to 1A to 2B.

D. Reproductive organs:

*Androecium.*—Present on disc florets only; no pollen.

*Gynoecium.*—Present on both ray and disc florets.

PLANT

A. General appearance:

*Height.*—Tall; 25 to 35 cm as a pinched pot mum with 0 to 7 long days after pinch prior to short days and 1 to 2 applications of 2500 ppm B-9 SP.

*Branching pattern.*—Upright and prolific.

B. Foliage:

*Color (upper surface).*—147A to 147B.

*Color (under surface).*—147B to 147C.

*Shape.*—Deeply lobed and slightly serrated.

CHART A

Comparison of Dare and Echo

| Cultivar | Ray Floret Color | Capitulum Form and Type | Branching Pattern |
|---|---|---|---|
| Dare | White | Flat Spooned Anemone | Upright and prolific |
| Echo | Ivory White | Flat Spooned Anemone | Upright |

| Cultivar | Diameter across face of capitulum | Plant height | Flowering response period |
|---|---|---|---|
| Dare | Up to 14 cm as disbud | Tall | 8 weeks |
| Echo | 70–75 mm as spray | Medium | 9 weeks |

| Cultivar | Recommended Use |
|---|---|
| Dare | Disbud and spray |
| Echo | Spray only |

Comparisons made of plants grown as pinched pot mums (Dare as disbud, Echo as spray) in Salinas, California

I claim:

1. A new and distinct Chrysanthemum plant named Dare, as described and illustrated, and parts thereof.

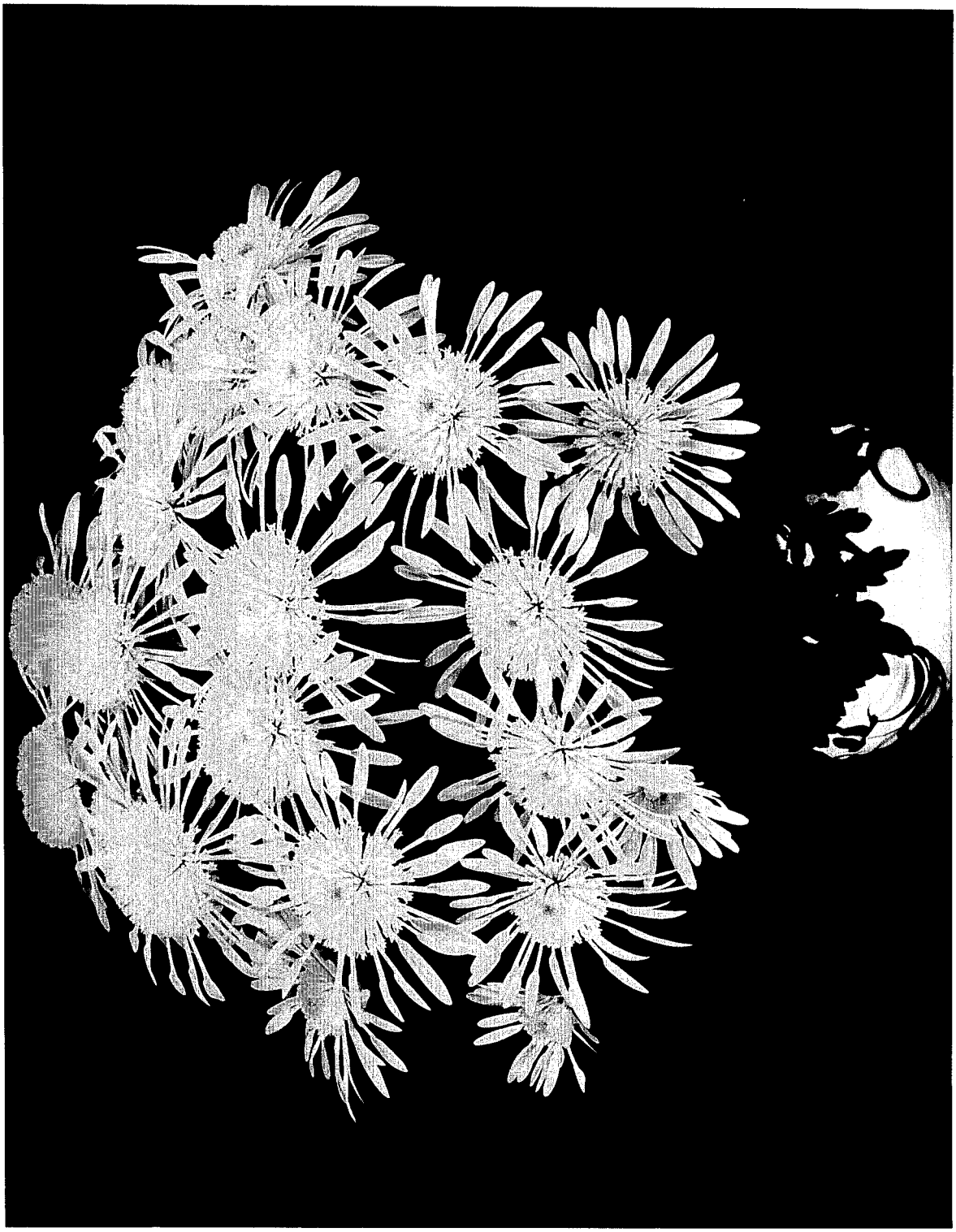

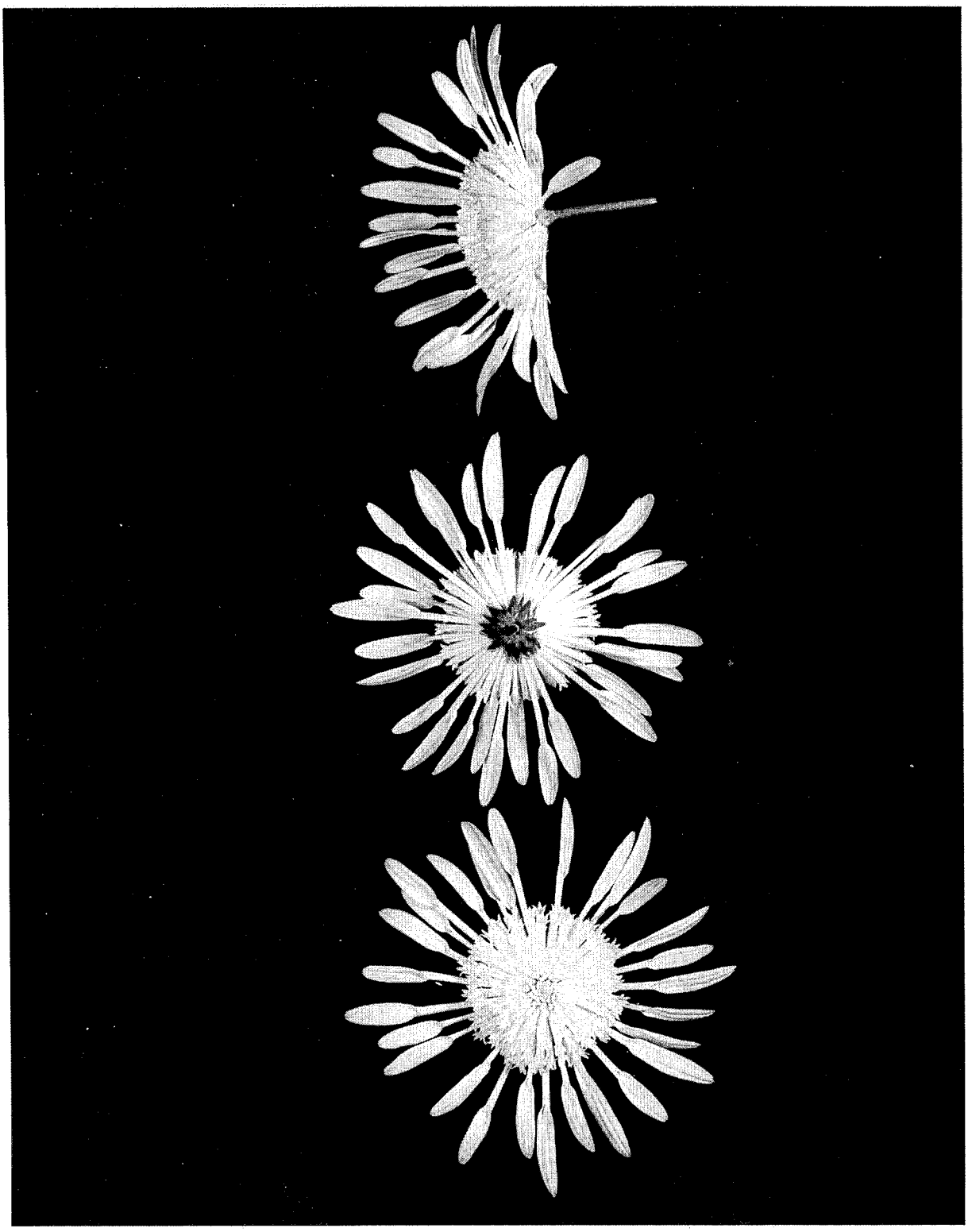

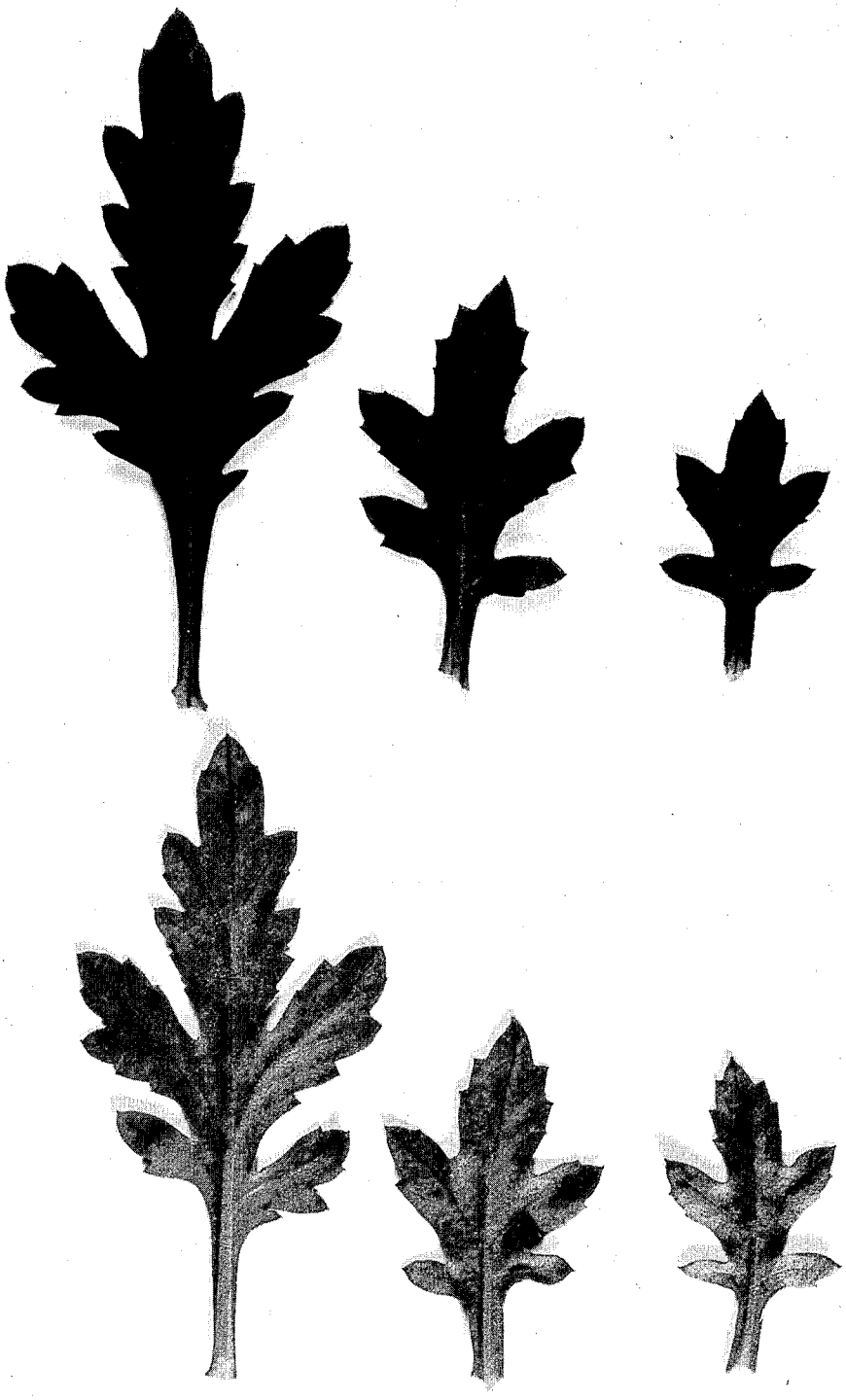

* * * * *